United States Patent [19]

Nikles et al.

[11] 4,344,877

[45] Aug. 17, 1982

[54] BICYCLO 4-ACYLOXYPIPERIDINE LIGHT STABILIZERS

[75] Inventors: Erwin Nikles, Liestal; Friedrich Karrer, Zofingen, both of Switzerland

[73] Assignee: Ciba-Geigy Corporation, Ardsley, N.Y.

[21] Appl. No.: 224,859

[22] Filed: Jan. 14, 1981

Related U.S. Application Data

[63] Continuation of Ser. No. 92,890, Nov. 9, 1979, abandoned, which is a continuation of Ser. No. 880,662, Feb. 23, 1978, abandoned.

[30] Foreign Application Priority Data

Feb. 24, 1977 [CH] Switzerland ............ 2309/77

[51] Int. Cl.³ .................. C08K 5/34; C07D 401/14; C07D 401/12
[52] U.S. Cl. .................. 524/102; 546/187; 546/188; 546/205; 546/222; 524/103
[58] Field of Search ........... 546/187, 188, 205, 222; 260/45.8 N, 45.8 NP

[56] References Cited

U.S. PATENT DOCUMENTS

| | | | |
|---|---|---|---|
| 4,031,095 | 6/1977 | Ramey et al. | 546/222 |
| 4,056,507 | 11/1977 | Ramey et al. | 260/45.8 NP |
| 4,089,842 | 5/1978 | Ramey et al. | 260/45.8 NP |
| 4,096,199 | 1/1978 | Ramey et al. | 260/45.8 NP |
| 4,101,508 | 7/1978 | Minagawa et al. | 260/45.8 NP |
| 4,101,509 | 7/1978 | Ramey et al. | 260/45.8 NP |
| 4,191,682 | 3/1980 | Ramey et al. | 260/45.8 NP |

FOREIGN PATENT DOCUMENTS

| | | | |
|---|---|---|---|
| 2627688 | 1/1977 | Fed. Rep. of Germany | 546/222 |
| 51-126385 | 11/1976 | Japan | 546/222 |

*Primary Examiner*—Robert T. Bond
*Attorney, Agent, or Firm*—Luther A. R. Hall

[57] ABSTRACT

A 4-acyloxypiperidine of the formula I

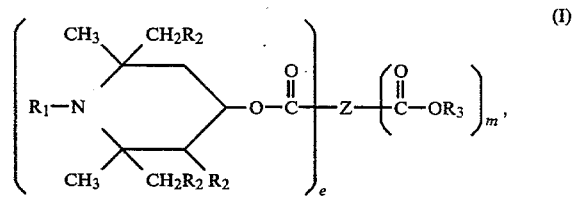

in which $R_1$ denotes $C_1$–$C_{30}$-alkyl, $C_3$–$C_{20}$-alkenyl, $C_3$–$C_{20}$-alkynyl, $C_2$–$C_{30}$-cyanoalkyl, $C_2$–$C_{30}$-alkoxyalkyl, $C_7$–$C_{20}$-aralkyl, 2,3-epoxypropyl, an aliphatic, alicyclic, aromatic, araliphatic or heterocyclic acyl group with 1-20 C atoms or one of the groups —$CH_2COOR_4$, —$CH_2$-$CH(R_5)$—$OR_6$, —$COOR_7$ or —$CONHR_7$, in which $R_4$ is $C_1$–$C_{12}$-alkyl, $C_3$–$C_6$-alkenyl, phenyl, $C_7$–$C_8$-aralkyl or cyclohexyl and $R_5$ is hydrogen, methyl or phenyl and $R_6$ denotes hydrogen or an aliphatic or aromatic, araliphatic or alicyclic acyl group with 1-18 C atoms, in which the aromatic part can optionally be substituted by chlorine, $C_1$–$C_4$-alkyl or $C_1$–$C_8$-alkoxy and/or by hydroxyl, and $R_7$ denotes $C_1$–$C_{12}$-alkyl, cyclohexyl, phenyl or benzyl, $R_2$ is hydrogen or $C_1$–$C_8$-alkyl, $R_3$ is $C_1$–$C_{30}$-alkyl, $C_1$–$C_{30}$-hydroxyalkyl, $C_2$–$C_{30}$-cyanoalkyl, $C_2$–$C_{30}$-alkoxyalkyl, $C_3$–$C_{30}$-alkoxycarbonylalkyl, $C_3$–$C_{20}$-alkenyl, $C_3$–$C_{20}$-alkynyl, $C_3$–$C_{12}$-cycloalkyl, $C_6$–$C_{15}$-aryl or $C_7$–$C_{20}$-aralkyl, Z is a monovalent to tetravalent 6-membered cycloaliphatic radical with a $C_1$–$C_2$ bridge member, e is 1-4, m is 0-3 and e+m is 1-4, as stabilizers for organic material.

9 Claims, No Drawings

BICYCLO 4-ACYLOXYPIPERIDINE LIGHT STABILIZERS

This is a continuation of application Ser. No. 92890, filed Nov. 9, 1979, now abandoned, which in turn is a continuation of application Ser. No. 880,662, filed on Feb. 23, 1978, now abandoned.

The invention relates to new 4-acyloxypiperidines, their manufacture and their use as stabilisers for plastics and to the material stabilised with these compounds.

It is known from Japanese Published Specification No. 51-126,385 that compounds of the di-2',2',6',6'-tetramethyl-4'-piperidyl 5-norbornene-2,3-dicarboxylate (compound No. 1 in the cited specification) type, which are unsubstituted or N-oxidised on the piperidine N-atom protect organic material, such as polyolefines, against the harmful influence of UV light. However, the use of such stabilisers leads to discolorations in the substrate.

The object of the present invention was to provide stabilisers which do not have this disadvantage or have this disadvantage to only a considerably lesser extent.

Accordingly, the invention relates to new 4-acyloxypiperidines of the formula I

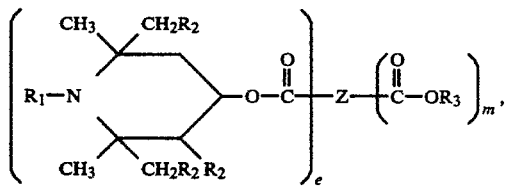

in which $R_1$ denotes $C_1$–$C_{30}$-alkyl, $C_3$–$C_{20}$-alkenyl, $C_3$–$C_{20}$-alkynyl, $C_2$–$C_{30}$-cyanoalkyl, $C_2$–$C_{30}$-alkoxyalkyl, $C_7$–$C_{20}$-aralkyl, 2,3-epoxypropyl, an aliphatic, alicyclic, aromatic, araliphatic or heterocyclic acyl group with 1–20 C atoms or one of the groups —$CH_2COOR_4$, —$CH_2$—$CH(R_5)$—$OR_6$, —$COOR_7$ or —$CONHR_7$, in which $R_4$ is $C_1$–$C_{12}$-alkyl, $C_3$–$C_6$-alkenyl, phenyl, $C_7$–$C_8$-aralkyl or cyclohexyl and $R_5$ is hydrogen, methyl or phenyl and $R_6$ denotes hydrogen or an aliphatic or aromatic, araliphatic or alicyclic acyl group with 1-18 C atoms, in which the aromatic part can optionally be substituted by chlorine, $C_1$–$C_4$-alkyl or $C_1$–$C_8$-alkoxy and/or by hydroxyl, and $R_7$ denotes $C_1$–$C_{12}$-alkyl, cyclohexyl, phenyl or benzyl, $R_2$ is hydrogen or $C_1$–$C_8$-alkyl, $R_3$ is $C_1$–$C_{30}$-alkyl, $C_1$–$C_{30}$-hydroxyalkyl, $C_2$–$C_{30}$-cyanoalkyl, $C_2$–$C_{30}$-alkoxyalkyl, $C_3$–$C_{30}$-alkoxycarbonylalkyl, $C_3$–$C_{20}$-alkenyl, $C_3$–$C_{20}$-alkynyl, $C_3$–$C_{12}$-cycloalkyl, $C_6$–$C_{15}$-aryl or $C_7$–$C_{20}$-aralkyl, Z is a monovalent to tetravalent 6-membered cycloaliphatic radical with a $C_1$–$C_2$ bridge member, e is 1–4, m is 0–3 and e+m is 1–4.

As $C_1$–$C_8$-alkyl, $R_2$ is branched or, in particular, unbranched alkyl, such as ethyl, n-propyl or n-butyl, but above all methyl. $R_2$ is preferably hydrogen. All the substituents $R_2$ are identical.

As $C_1$–$C_{30}$-alkyl, $R_1$ is, for example, methyl, ethyl, n-propyl, n-butyl, n-pentyl, n-hexyl, n-octyl, n-decyl or n-dodecyl. Preferred alkyl groups are those with 1–8 C atoms, especially those with 1–4 C atoms and above all methyl.

As $C_3$–$C_{20}$-alkenyl, $R_1$ is, in particular, alkenyl with 3–6 C atoms, for example allyl, 2-butenyl or 2-hexenyl, especially allyl.

As $C_3$–$C_{20}$-alkynyl, $R_1$ is, in particular, alkynyl with 3–4 C atoms, for example propargyl.

As $C_2$–$C_{20}$-cyanoalkyl, $R_1$ is, in particular, cyanoalkyl with 2–8 C atoms, such as cyanomethyl.

If $R_1$ denotes $C_2$–$C_{30}$-alkoxyalkyl, the alkyl part can contain, in particular, 1–3 C atoms and the alkoxy part can consist, in particular, of 1–18 C atoms, such as, for example, in methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl. Compounds in which $R_1$ denotes an alkoxyalkyl group with 2–6 C atoms are to be mentioned in particular.

As $C_7$–$C_{20}$-aralkyl, $R_1$ is, for example, benzyl or α-phenylethyl, which is optionally substituted by $C_1$–$C_8$-alkoxy but above all is unsubstituted.

As an aliphatic acyl group with 1–20 C atoms, $R_1$ is, in particular, an aliphatic acyl group with 1–4 C atoms, for example formyl, acetyl, acryloyl or crotonyl, especially acetyl or formyl.

As an aromatic acyl group, $R_1$ is, in particular, an aromatic acyl group with 7–20 C atoms and as an araliphatic acyl group $R_1$ is, in particular, an araliphatic acyl group with 8–20 C atoms, such as phenyl-, phenylmethyl- or phenylethylcarbonyl, which can be substituted in the phenyl part, such as by 2 $C_1$–$C_8$-alkyl groups and a hydroxyl group, such as 4-hydroxy-3,5-di-tert.-butyl-benzoyl, 4-hydroxy-3,5-di-tert.-butyl-phenylacetyl or β-(4-hydroxy-3,5-di-tert.-butyl-phenyl)propionyl.

As heterocyclic acyl, $R_1$ is, in particular, heterocyclic acyl with 5–20 C atoms, such as pyridylcarbonyl.

If $R_1$ is the group —$CH_2COOR_4$, $R_4$, as $C_1$–$C_{12}$-alkyl, denotes, for example, methyl, ethyl, isopropyl, n-butyl, isobutyl, t-butyl, isopentyl, n-octyl, n-decyl or n-dodecyl. $R_4$ is preferably $C_1$–$C_4$-alkyl. As $C_3$–$C_6$-alkenyl, $R_4$ is, for example, allyl, 2-butenyl or 2-hexenyl. As $C_7$–$C_8$-aralkyl, $R_4$ is, for example, benzyl or α-phenylethyl.

If $R_1$ is the group —$CH_2CH(R_5)$-$OR_6$, $R_5$ denotes hydrogen, methyl or phenyl, especially hydrogen. As an aliphatic, aromatic, alicyclic or araliphatic $C_1$–$C_{18}$-acyl radical which is optionally substituted in the aromatic part by chlorine, by $C_1$–$C_4$-alkyl, such as methyl, ethyl, n-propyl or t-butyl, or by $C_1$–$C_8$-alkoxy, such as methoxy, ethoxy, butoxy or octoxy, and/or by hydroxyl, $R_6$ is, for example, acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)propionyl, phenylacetyl, cinnamoyl or hexahydrobenzoyl.

If $R_1$ is the group —$COOR_7$, $R_7$, as $C_1$–$C_{12}$-alkyl, is, for example, methyl, ethyl, isobutyl, n-hexyl, n-octyl, n-decyl or n-dodecyl. Alkyl groups with 1–4 C atoms are preferred as $R_7$. The same applies in the case of $R_7$ in —$CONHR_7$.

As alkyl, hydroxyalkyl, cyanoalkyl, alkoxyalkyl, alkenyl, alkynyl and aralkyl, $R_3$ preferably has the meanings indicated for $R_1$. As $C_3$–$C_{30}$-alkoxycarbonylalkyl, $R_3$ is, in particular, as indicated for —$CH_2COOR_4$. As $C_3$–$C_{12}$-cycloalkyl, $R_3$ is, in particular, $C_5$–$C_6$-cycloalkyl, such as cyclopentyl and especially cyclohexyl. As $C_6$–$C_{15}$-aryl, $R_3$ is, in particular, phenyl.

As a monovalent to tetravalent 6-membered cycloaliphatic radical with a $C_1$–$C_2$ bridge member, Z is, in particular, a cyclohexyl or cyclohexenyl radical which is bridged by methylene, ethylene or ethenylene, such as a radical of bicyclo[2.2.1]heptane, bicyclo[2.2.1]hept-5-ene, bicyclo[2.2.2]octane or bicyclo[2.2.2]oct-5-ene, it being possible for such radicals also to be monosubstituted or polysubstituted by $C_1$–$C_4$-alkyl, such as methyl or isopropyl, or halogen, such as chlorine, such as 1,2,2,3,4,5-hexachloro-bicyclo[2.2.1]heptane or methyl-bicyclo[2.2.1]hept-5-ene.

Piperidines of the formula I in which $R_1$ is $C_1$–$C_{20}$-alkyl, $C_3$–$C_5$-alkenyl, $C_3$–$C_5$-alkynyl or $C_7$–$C_{20}$-aralkyl, $R_2$ is hydrogen or methyl, $R_3$ is $C_1$–$C_{20}$-alkyl, Z is a monovalent to tetravalent radical of bicyclo[2.2.1]heptane or bicyclo[2.2.1]-hept-5-ene which is optionally substituted by $C_1$–$C_4$-alkyl or chlorine, e is 1–4, m is 0–3 and e+m is 1–4 are preferred.

Piperidines of the formula I in which $R_1$ is $C_1$–$C_8$-alkyl or benzyl, $R_2$ is hydrogen, Z is a monovalent or divalent radical of bicyclo[2.2.1]heptane or bicyclo[2.2.1]hept-5-ene which is optionally substituted by $C_1$–$C_4$-alkyl, e is 1 or 2 and m is 0 are particularly preferred, as are also the piperidines mentioned in the examples.

To be particularly mentioned are also:
bis-(1,2,2,6,6-pentamethyl-4-piperidyl) bicyclo[2.2.1]hept-5-ene-cis,endo-2,3-dicarboxylate,
bis-(1,2,2,6,6-pentamethyl-4-piperidyl) bicyclo[2.2.1]hept-5-ene-cis,exo-2,3-dicarboxylate,
bis-(1-benzyl-2,2,6,6-tetramethyl-4-piperidyl) bicyclo[2.2.1]-hept-5-ene-cis,endo-2,3-dicarboxylate,
bis-(1-benzyl-2,2,6,6-tetramethyl-4-piperidyl) bicyclo[2.2.1]hept-5-ene-cis,exo-2,3-dicarboxylate,
bis-(1,2,2,6,6-pentamethyl-4-piperidyl) bicyclo[2.2.1]heptane-cis,endo-2,3-dicarboxylate,
bis-(1,2,2,6,6-pentamethyl-4-piperidyl) bicyclo[2.2.1]heptane-cis,exo-2,3-dicarboxylate,
bis-(1-benzyl-2,2,6,6-tetramethyl-4-piperidyl) bicyclo[2.2.1]heptane-cis,endo-2,3-dicarboxylate,
bis-(1-benzyl-2,2,6,6-tetramethyl-4-piperidyl) bicyclo[2.2.1]heptane-cis,exo-2,3-dicarboxylate.

In the case of the bicyclo-heptane derivatives and bicyclooctane derivatives, stereoisomers are possible; thus, for example, in the case of α,β-dicarboxylic acid derivatives, (cis)-endo, (cis)-exo and endo,exo forms are possible. The products can be mixtures of stereoisomers, such as can occur in a synthesis. For industrial purposes it is not necessary, although possible in the customary manner, to isolate the pure isomers.

The piperidines of the formula I can be manufactured according to methods known per se, e.g. by reacting a 4-OH-piperidine of the formula II

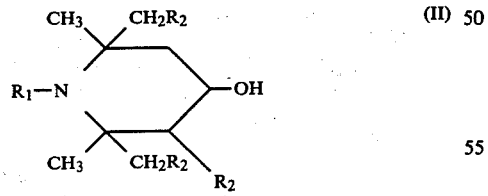
(II)

with a reactive derivative of a carboxylic acid of the formula III

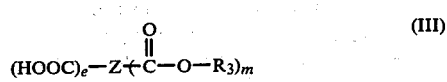
(III)

in which $R_1$, $R_2$, $R_3$, Z, e and m have the above meaning.

A reactive derivative of a carboxylic acid of the formula III is, in particular, an ester, such as a $C_1$–$C_{12}$-alkyl ester, for example a methyl ester, and the reaction is carried out, in particular, in the presence of a basic catalyst, such as an alkali metal alcoholate, such as sodium methylate, and optionally in solution, such as in an inert solvent, such as xylene, toluene or the like.

Another procedure which can be employed for the manufacture of piperidines of the formula I in which Z is a bicyclo[2.2.1]hept-5-ene is to react a corresonding acrylate of a piperidine of the formula II, such as the methacrylate, with cyclopentadiene, in particular at elevated temperature and optionally in an inert solvent, such as benzene.

The starting materials are known or, if they are new, can be manufactured analogously to known compounds. Piperidinols of the formula II are described in DT-OS No. 2,352,658 ($R_2$ is hydrogen) and DT-OS No. 2,623,422 ($R_2$ is lower alkyl). Carboxylic acid derivatives of the formula III are known, inter alia, from Japanese Published Specification No. 51-126,385.

According to the present invention, the compounds of the formula I can be used as stabilisers for plastics in order to protect them against damage due to the action of oxygen, heat and light. Examples of such plastics are the polymers listed on pages 12–14 of DT-OS No. 2,456,864.

The stabilising of polyolefines and styrene polymers and of polyurethanes is particularly important and the piperidines of the formula I are outstandingly suitable for this. Examples of such polymers are high density and low density polyethylene, polypropylene, ethylene/propylene copolymers, polystyrene, styrene/butadiene/acrylonitrile copolymers, mixtures of polyolefines or of styrene polymers and polyurethanes based on polyethers or polyesters, in the form of lacquers, elastomers or foams.

The stabilisers are added to the plastics in a concentration of 0.01 to 5% by weight, calculated relative to the material to be stabilised. Preferably 0.03 to 1.5, and particularly preferentially 0.2 to 0.6, % by weight of the compounds, calculated relative to the material to be stabilised, are incorporated into the latter.

Incorporation can be effected after polymerisation, for example by mixing the compounds, and optionally further additives, into the melt by the methods customary in the art, before or during shaping, or also by applying the dissolved or dispersed compounds to the polymer, with subsequent evaporation of the solvents if necessary.

The new compounds can also be added to the plastics to be stabilised in the form of a master batch which contains these compounds, for example in a concentration of 2.5 to 25% by weight.

In the case of crosslinked polyethylene, the compounds are added prior to crosslinking.

In addition to the compounds of the formula I, yet further known stabilisers can also be added to the plastics. These stabilisers can be, for example, antioxidants, light stabilisers or metal deactivators or also co-stabilisers such as, for example, those of the phosphorous acid ester type. Furthermore, other additives customary in plastics technology, such as, for example, flameproofing agents, antistatic agents, plasticisers, lubricants, blowing agents, pigments, reinforcing materials or fillers, can also be added. Examples of additives which can be used together with the compounds of the formula I are given on pages 18–24 of DT-OS No. 2,427,853.

The invention therefore also relates to plastics which have been stabilised by the addition of 0.01 to 5% by weight of a compound of the formula I and which optionally can contain yet further known and customary additives. The plastics stabilised in this way can be used in very diverse forms, for example as films, fibres, tapes or profiles or as binders for lacquers, adhesives or putties.

The manufacture and use of the compounds according to the invention is described in more detail in the following Examples. In these Examples, parts are parts by weight and percentages are percent by weight. The temperatures are given in degrees Centigrade.

EXAMPLE 1

(1,2,2,6,6-Pentamethyl-4-piperidyl)
2-methyl-bicyclo[2.2.1]hept-5-ene-2-carboxylate
(which can be designated also as
1'-methyl-2',2',6',6'-tetramethyl-4'-piperidyl
2-methyl-5-norbornene-2-carboxylate)

A mixture of 60 g of 1-methyl-2,2,6,6-tetramethyl-4-piperidyl methacrylate, 80 ml of cyclopentadiene and 50 ml of benzene is refluxed. After 5 hours, a further 30 ml of cyclopentadiene are added, and the solution is subsequently kept at the boiling point for a further 2 hours. The solvent and the unreacted cyclopentadiene are distilled off, and the residue is fractionated under high vacuum, b.p. 132°–133°/0.4 mm Hg.

The 1-methyl-2,2,6,6-tetramethyl-4-piperidinyl-methacrylate used as starting material is obtained according to U.S. Pat. No. 3,705,166.

EXAMPLE 2

Tetra-(1-benzyl-2,2,6,6-tetramethyl-4-piperidyl bicyclo[2.2.2]oct-7-ene-2,3,5,6-tetracarboxylate 80 mg of lithium amide are added, with stirring, to a solution, heated to about 125°, of 17 g of tetramethyl bicyclo [2.2.2]oct-7-ene-2,3,5,6-tetracarboxylate (m.p. 130°–131°; produced from bicyclo[2.2.2]oct-7-ene-2,3,5,6-tetracarboxylic acid-2,3,5,6-dianhydride by complete esterification with methanol in the presence of a catalytic amount of concentrated sulphuric acid) and 49.5 g of 1-benzyl-2,2,6,6-tetramethyl-4-piperidinol in 300 ml of anhydrous xylene. The reaction mixture is then heated, with the continuous passing through of a slight flow of nitrogen, in the course of about 3 hours to 135°, with the liberated methanol and also xylene being distilled off through the mounted descending condenser. A further 30 mg of lithium amide are thereupon added and the internal temperature is gradually raised to 150°, with the xylene being distilled off as completely as possible (total reaction time about 21 hours). For processing, the reaction mixture is cooled to about 70° C.; 200 ml of methanol are then added, and the mixture is thoroughly stirred, in the course of which the crude product precipitates as a resinous substance. The supernatant methanol is immediately decanted; the resin residue is dissolved hot in the smallest possible amount of 2-propanol, and slowly cooled to room temperature with stirring. The supernatant 2-propanol is again decanted; the residue is then triturated, in a mortar, with a small amount of cold methanol into the form of a fine (amorphous) powder, which is collected on a suction filter. The virtually colourless tetra-(1-benzyl-2,2,6,6-tetramethyl-4-piperidyl) bicyclo[2.2.2]oct-7-ene-2,3,5,6-tetracarboxylate obtained in this manner is dried in vacuo at 40°.

Elementary analysis
calculated: C: 75.96%; H: 8.72%; N: 4.66%; O: 10.65%; found: C: 75.8%; H: 8.8%; N: 4.7%; O: 10.5%.

EXAMPLE 3

Tetra-(1,2,2,6,6-pentamethyl-4-piperidyl) bicyclo[2.2.2]oct-7-ene-2,3,5,6-tetracarboxylate In a manner analogous to that described in Example 2, there is produced from tetramethyl bicyclo[2.2.2]oct-7-ene-2,3,5,6-tetracarboxylate and 1,2,2,6,6-pentamethyl-4-piperidinol, by transesterification in xylene with lithium amide as catalyst, tetra-(1,2,2,6,6-pentamethyl-4-piperidyl bicyclo[2.2.2]oct-7-ene-2,3,5,6-tetracarboxylate as amorphous colourless powder.

Elementary analysis
calculated: C: 69.61%; H: 9.89%; N: 6.24%; found: C: 69.4%; H: 10.0%; N: 6.1%.

EXAMPLES 4–10

Bis-(1-benzyl-2,2,6,6-tetramethyl-4-piperidyl bicyclo[2.2.1]heptane-endo,exo-2,3-dicarboxylate (Example 4)

The Diels-Alder adduct from cyclopentadiene and dimethyl maleate is catalytically hydrogenated in the known manner. 21.2 g of the resulting mixture of the stereoisomeric cis-endo-and cis-exo-dimethyl bicyclo[2.2.1]heptane-dicarboxylates are heated in the presence of 1 g of lithium amide, with stirring, with 49.4 g of 1-benzyl-2,2,6,6-tetramethyl-4-piperidinol in 50 ml of xylene for 16 hours at about 130°–150°. The methanol formed is continuously distilled off. The entire amount of solvent is subsequently removed in vacuo, and the residue is crystallised from isopropanol, m.p. 149°–151°. On the basis of the NMR spectrum, the product obtained is the pure endo,exo isomer.

Elementary analysis
calculated: C: 76.60%; H: 9.09%; N: 4.36%; found: C: 76.34%; H: 8.94%; N: 4.05%.

In an analogous manner, the mixture of stereoisomeric cis-endo- and cis-exo-dimethyl bicyclo[2.2.1]hept-5-ene-2,3-dicarboxylates is reacted with the following N-substituted 2,2,6,6-tetramethyl-4-piperidinol derivatives:

1,2,2,6,6-Pentamethyl-4-piperidinol: resin
Elementary analysis
calculated: C: 71.27%; H: 9.90%; N: 5.73%; found: C: 71.10%; H: 9.75%; N: 5.53%: (Example 5).

1-Allyl-2,2,6,6-tetramethyl-4-piperidinol: resin
Elementary analysis
calculated: C: 73.29%; H: 9.69%; N: 5.18%; found: C: 73.22%; H: 9.71%; N: 5.08%. (Example 6).

1-n-Octyl-2,2,6,6-tetramethyl-4-piperidinol
Elementary analysis
calculated: C: 75.39%; H: 11.18%; N: 4.09%; found: C: 73.76%; H: 11.12%; N: 4.07%. (Example 7).

1-n-Dodecyl-2,2,6,6-tetramethyl-4-piperidinol
Elementary analysis
calculated: C: 76.83%; H: 11.63%; N: 3.51%; found: C: 75.77%; H: 11.90%; N: 3.72%. (Example 8).

In an analogous manner is also reacted diethyl bicyclo [2.2.1]hept-5-ene-endo,exo-2,3-dicarboxylate with 1-n-octadecyl-2,2,6,6-tetramethyl-4-piperidinol to give wax-like bis-(1-n-octadecyl-2,2,6,6-tetramethyl-4-piperidyl) bicyclo[2.2.1]hept-5-ene-endo,exo-2,3-dicarboxylate. (Example 9)
Elementary analysis calculated: C: 78.36%; H: 12.11%; N: 2.90%; found: C: 77.9%; H: 12.5%; N: 3.0%.

There can also be produced analogously: bis-(1-benzyl-2,2,6,6-tetramethyl-4-piperidinyl) bicyclo[2.2.1-]hept-5-ene-endo,exo-2,3-dicarboxylate, m.p. 128°–130°. (Example 10)

Elementary analysis
calculated: C: 76.71%; H: 8.96%; N: 4.36%; found: C: 76.74%; H: 8.94%; N: 4.39%.

EXAMPLES 11 AND 12

Bis-(1,2,2,6,6-pentamethyl-4-piperidyl) bicyclo[2.2.1]heptane-endo,exo-2,3-dicarboxylate (Example 11)

30 g of diethyl bicyclo[2.2.1]heptane-endo,exo-2,3-dicarboxylate (obtained in a known manner by catalytic hydrogenation of the adduct of diethyl fumarate with cyclopentadiene) and 47 g of 1,2,2,6,6-pentamethyl-4-piperidinol are heated in the presence of 100 ml of xylene and 1 ml of tetrabutylorthotitanate for 16 hours at about 130°. The formed ethanol is continuously distilled off. At the end of the reaction, the xylene is distilled off, finally in vacuo at 0.02 mm Hg and 150°. The product remains behind as resin.

Elementary analysis
calculated: C: 70.98%; H: 10.27%; N: 5.71%; O: 13.04%; found: C: 70.81%; H: 10.21%; N: 5.59%; O: 13.44%.

It is possible to produce in an analogous manner: bis-[1-(2-propin-1-yl)-2,2,6,6-tetramethyl-4-piperidyl] bicyclo [2.2.1]hept-5-ene-endo,exo-2,3,-dicarboxylate; resin (Example 12)

Elementary analysis
calculated: C: 73.84%; H: 9.01%; N: 5.22%; found: C: 73.66%; H: 9.09%; N: 5.25%.

EXAMPLES 13 AND 14

Bis-(1-phenylcarbamoyl-2,2,6,6-tetramethyl-4-piperidyl) bicyclo [2.2.1]hept-5-ene-endo,exo-2,3-dicarboxylate (Example 13)

44 ml of phenylisocyanate, dissolved in 50 ml of toluene, are added portionwise to 92 g of bis-(2,2,6,6-tetramethyl-4-piperidyl) bicyclo[2.2.1]hept-5-ene-endo,exo-2,3-dicarboxylate. The mixture is held at 70° for 16 hours; it is subsequently refluxed for 4 hours, and then allowed to crystallise at room temperature. The product is filtered off, and extracted with hot hexane, m.p. 131°–133°.

Elementary analysis
calculated: C: 70.46%; H: 7.79%; N: 8.02%; found: C: 70.75%; H: 7.91%; N: 8.05%.

It is possible in a similar manner to react bis-(2,2,6,6-tetramethyl-4-piperidyl) bicyclo[2.2.1]heptane-endo,exo-2,3-dicarboxylate with phenylisocyanate, m.p. 118°–120° (Example 14)

EXAMPLE 15

Bis-(1-acryloyl-2,2,6,6-tetramethyl-4-piperidyl) bicyclo [2.2.1]hept-5-ene-endo,exo-2,3-dicarboxylate 46.4 g of bis-(2,2,6,6-tetramethyl-4-piperidyl) bicyclo[2.2.1]hept-5-ene-endo,exo-2,3-dicarboxylate are dissolved in 200 ml of anhydrous toluene, and to the solution are added dropwise at room temperature 19 g of acrylic acid chloride. The temperature is subsequently raised to 50° and 21.2 g of triethylamine are slowly added. The mixture is stirred for 24 hours at 50° and then filtered. The triethylamine hydrochloride which has been filtered off is washed with toluene. The combined filtrates are concentrated by evaporation, and the residue is crystallised from ligroin, m.p. 138°–139°.

Elementary analysis
calculated: C: 69.69%; H: 8.51%; N: 4.92%; found: C: 69.68%; H: 8.56%; N: 5.21%.

EXAMPLE 16

Bis-(1-acetyl-2,2,6,6-tetramethyl-4-piperidyl) bicyclo[2.2.1]hept-5-ene-endo,exo-2,3-dicarboxylate 46 g of bis-(2,2,6,6-tetramethyl-4-piperidyl) bicyclo[2.2.1]hept-5-ene-endo,exo-2,3-dicarboxylate are dissolved in 200 ml of toluene, and to the solution are added 54 g of acetic anhydride. The solution is kept for 16 hours at 60°, and subsequently concentrated by evaporation. The resin-like residue is freed from volatile constituents at 80° and 0.1 mm Hg.

Elementary analysis
calculated: C: 68.35%; H: 8.88%; N: 5.14%; found: C: 68.6%; H: 9.2%; N: 5.6%.

EXAMPLE 17

Bis-(1,2,3,6-tetramethyl-2,6-diethyl-4-piperidyl) bicyclo[2.2.1]heptane-endo,exo-2,3-dicarboxylate 10.6 g of dimethyl bicyclo[2.2.1]heptane-2,3-dicarboxylate (mixture of about ⅔ cis-endo and ⅓ cis-exo) and 21.3 g of 1,2,3,6-tetramethyl-2,6-diethyl-4-piperidinol are heated in the presence of 1 g of lithium amide for 6 hours at 130°–140°. The formed methanol is continuously distilled off. The volatile parts at boiling point 185°/0.1 mm Hg are subsequently removed. The residue is dissolved in acetone, treated with charcoal, filtered, and concentrated by evaporation. The product is obtained as light-brown resin.

Elementary analysis
calculated: C: 73.1%; H: 10.8%; N: 4.9%; found: C: 72.2%; H: 10.6%; N: 4.8%.

EXAMPLE 18

Methyl bicyclo[2.2.1]hept-5-ene-2-carboxylate-(1-methyl-2,2,6,6-tetramethyl-4-piperidyl)-2-acetate 22.4 g of dimethyl bicyclo[2.2.1]hept-5-ene-2-carboxylic acid-2-acetate, 41 g of 1,2,2,6,6-pentamethyl-4-piperidinol and 1 g of lithium amide are kept for 18 hours at 130°–140°, and the formed methanol is continuously distilled off. The residue is taken up in acetonitrile and filtered; the filtrate is then concentrated by evaporation and the residue is distilled twice, b.p. 143°–148°/0.1 mm Hg.

Elementary analysis
calculated: C: 69.39%; H: 9.15%; N: 3.85%; found: C: 69.01%; H: 9.38%; N: 4.12%.

What is claimed is:

1. A 4-acyloxypiperidine compound of formula I

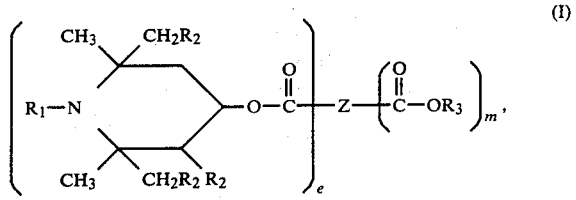

in which $R_1$ denotes $C_1$–$C_{30}$-alkyl; $C_3$–$C_{20}$-alkenyl; $C_3$–$C_{20}$-alkynyl; $C_2$–$C_{30}$-cyanoalkyl; $C_2$–$C_{30}$-alkoxyalkyl; benzyl, α-phenylethyl, or said benzyl or said α-phenylethyl substituted by $C_1$–$C_8$-alkoxy; 2,3-epoxypropyl; $C_1$–$C_{20}$-alkanoyl; $C_2$–$C_{20}$-alkenoyl; benzoyl, phenylacetyl, phenylpropionyl or said benzoyl, said phenylacetyl or said phenylpropionyl substituted on the phenyl ring by two $C_1$–$C_8$-alkyl and by a hydroxyl group; pyridylcarbonyl; or one of the groups —CH$_2$COOR$_4$, —CH$_2$—CH(R$_5$)—OR$_6$, —COOR$_7$ or —CONHR$_7$, in which $R_4$ is $C_1$–$C_{12}$-alkyl, $C_3$–$C_6$-alkenyl, phenyl, benzyl, α-phenylethyl or cyclohexyl and $R_5$ is hydrogen, methyl or phenyl and $R_6$ denotes hydrogen; $C_1$–$C_{18}$-alkanoyl; acryloyl; hexahydrobenzoyl; benzoyl, phenylacetyl, phenylpropionyl, or said benzoyl, said phenylacetyl or said phenylpropionyl substituted on the phenyl ring by chlorine, by $C_1$–$C_4$-alkyl, by $C_1$–$C_8$-alkoxy, by hydroxyl or by mixtures of said substituents; or cinnamoyl, and $R_7$ denotes $C_1$–$C_{12}$-alkyl, cyclohexyl, phenyl or benzyl, $R_2$ is hydrogen or $C_1$–$C_8$-alkyl, $R_3$ is $C_1$–$C_{30}$-alkyl, $C_1$–$C_{30}$-hydroxyalkyl, $C_2$–$C_{30}$-cyanoalkyl, $C_2$–$C_{30}$-alkoxyalkyl, $C_3$–$C_{30}$-alkoxycarbonylalkyl, $C_3$–$C_{20}$-alkenyl, $C_3$–$C_{20}$-alkynyl, $C_3$–$C_{12}$-cycloalkyl, phenyl; or benzyl, α-phenylethyl or said benzyl or said α-phenylethyl substituted by $C_1$–$C_8$-alkoxy, Z is a divalent or tetravalent radical of bicyclo[2.2.1]heptane, bicyclo[2.2.1]hept-5-ene, bicyclo[2.2.2]octane or bicyclo[2.2.2]oct-5-ene or said radical substituted by $C_1$–$C_4$-alkyl or chlorine, e is 2 or 4, m is 0 or 2, and e+m is 2 or 4.

2. A compound according to claim 1 in which $R_1$ is $C_1$–$C_{20}$-alkyl, $C_3$–$C_5$-alkenyl, $C_3$–$C_5$-alkynyl or benzyl, α-phenylethyl or said benzyl or said α-phenylethyl substituted by $C_1$–$C_8$-alkoxy, $R_2$ is hydrogen or methyl, $R_3$ is $C_1$–$C_{20}$-alkyl, Z is a divalent or tetravalent radical of bicyclo[2.2.1]heptane or bicyclo[2.2.1]hept-5-ene or said radical substituted by $C_1$–$C_4$-alkyl or chlorine, e is 2 or 4 m is 0 or 2 and e+m is 2 or 4.

3. A compound according to claim 1 in which $R_1$ is $C_1$–$C_{18}$-alkyl, allyl, propargyl, benzyl, acetyl, acryloyl or —CONH-phenyl, $R_2$ is hydrogen or methyl, $R_3$ is methyl, e is 2 or 4, m is 0, and e+m is 2 or 4.

4. A compound according to claim 1, in which $R_1$ is $C_1$–$C_8$-alkyl or benzyl, $R_2$ is hydrogen, Z is a divalent radical of bicyclo[2.2.1]heptane or bicyclo[2.2.1]-hept-5-ene on said radical substituted by $C_1$–$C_4$-alkyl, e is 2 and m is 0.

5. A compound according to claim 1 which is tetra-(1,2,2,6,6-pentamethyl-4-piperidyl) bicyclo[2.2.2]oct-7-ene-2,3,5,6-tetracarboxylate.

6. A compound according to claim 1 which is bis-(1-benzyl-2,2,6,6-tetramethyl-4-piperidyl) bicyclo[2.2.1]hept-5-ene-2,3-dicarboxylate.

7. A compound according to claim 1 which is bis-(1,2,2,6,6-pentamethyl-4-piperidyl) bicyclo[2.2.1]hept-5-ene-2,3-dicarboxylate.

8. A composition of a synthetic polymer subject to degradation by the active of ultraviolet light which contains an effective amount of a stabilizer compound according to claim 1.

9. A process for stabilizing a synthetic polymer subject to degradation by the action of ultraviolet light which comprises incorporating therein an effective amount of a stabilizer compound according to claim 1.

* * * * *